US009456743B2

(12) United States Patent
Sato et al.

(10) Patent No.: US 9,456,743 B2
(45) Date of Patent: Oct. 4, 2016

(54) IMAGE PROCESSING APPARATUS AND IMAGE PROCESSING METHOD

(71) Applicant: CANON KABUSHIKI KAISHA, Tokyo (JP)

(72) Inventors: Makoto Sato, Tokyo (JP); Hiroyuki Shinbata, Tama (JP)

(73) Assignee: Canon Kabushiki Kaisha, Tokyo (JP)

( * ) Notice: Subject to any disclaimer, the term of this patent is extended or adjusted under 35 U.S.C. 154(b) by 277 days.

(21) Appl. No.: 14/061,222

(22) Filed: Oct. 23, 2013

(65) Prior Publication Data

US 2014/0118690 A1 May 1, 2014

(30) Foreign Application Priority Data

Oct. 25, 2012 (JP) ................................ 2012-235484

(51) Int. Cl.

*A61B 3/10* (2006.01)
*A61B 3/14* (2006.01)
*G01B 9/02* (2006.01)
*A61B 3/12* (2006.01)

(52) U.S. Cl.

CPC ............ *A61B 3/102* (2013.01); *G01B 9/0203* (2013.01); *G01B 9/02028* (2013.01); *G01B 9/02044* (2013.01); *G01B 9/02091* (2013.01); *A61B 3/12* (2013.01); *G01B 2290/45* (2013.01); *G01B 2290/70* (2013.01)

(58) Field of Classification Search

USPC ....... 351/200, 205, 206, 209, 211, 213, 221, 351/222, 224, 243, 244, 245, 246

See application file for complete search history.

(56) References Cited

U.S. PATENT DOCUMENTS

| | | | | |
|---|---|---|---|---|
| 2008/0123092 | A1* | 5/2008 | Hatori .................. | A61B 5/0062 356/300 |
| 2008/0291463 | A1 | 11/2008 | Milner et al. | |
| 2009/0247862 | A1 | 10/2009 | Meyer et al. | |
| 2009/0310083 | A1 | 12/2009 | Campbell et al. | |
| 2012/0194782 | A1 | 8/2012 | Imamura | |

(Continued)

FOREIGN PATENT DOCUMENTS

| | | | |
|---|---|---|---|
| CN | 102429635 | A | 5/2012 |
| EP | 1925253 | A1 | 5/2008 |
| EP | 2243420 | A1 | 10/2010 |

(Continued)

OTHER PUBLICATIONS

Pircher, M. et al., "Polarization sensitive optical coherence tomography in the human eye", Progress in Retinal Eye Research, Jun. 26, 2011, pp. 431-451, vol. 30.

(Continued)

*Primary Examiner* — Joseph P Martinez
*Assistant Examiner* — Brandi Thomas
(74) *Attorney, Agent, or Firm* — Canon U.S.A. Inc., IP Division

(57) ABSTRACT

An image processing apparatus configured to process a tomographic image indicating the polarization state of a subject, includes an acquisition unit configured to acquire a plurality of the tomographic images imaged at different times, an extraction unit configured to extract each depolarized area from the plurality of the tomographic images, and a display control unit configured to display information about each depolarized area on a display unit with the information associated with each other.

14 Claims, 10 Drawing Sheets

(56) References Cited

U.S. PATENT DOCUMENTS

2012/0249962 A1 10/2012 Uchida
2013/0107277 A1* 5/2013 Hirose .................. A61B 3/102
356/512

FOREIGN PATENT DOCUMENTS

| | | | |
|---|---|---|---|
| JP | 2008-029732 | A | 2/2008 |
| JP | 2011-189113 | A | 9/2011 |
| WO | 2005017826 | A2 | 2/2005 |
| WO | 2010122118 | A1 | 10/2010 |
| WO | 2012/004967 | A1 | 1/2012 |
| WO | 2012/012646 | A1 | 1/2012 |
| WO | 2012/068408 | A1 | 5/2012 |

OTHER PUBLICATIONS

Mujat, M. et al., "Retinal nerve fiber layer thickness map determined from optical coherence tomography images", Optics Express, Nov. 14, 2005, pp. 9480-9491, vol. 13, No. 23.

* cited by examiner

IMAGE PROCESSING APPARATUS AND IMAGE PROCESSING METHOD

BACKGROUND OF THE INVENTION

1. Field of the Invention

The present invention relates to an image processing apparatus and an image processing method for processing an image of a subject.

2. Description of the Related Art

An optical coherence tomography (OCT) using a multiple-wavelength lightwave interference can acquire a high resolution tomographic image of a sample (fundus in particular).

In recent years, an ophthalmologic OCT apparatus can acquire not only a normal OCT image in which the shape of a fundus tissue is captured but also a polarization OCT image captured using a polarization parameter (retardation and orientation), which is one of optical characteristics of the fundus tissue.

The polarization OCT can configure the polarization OCT image using the polarization parameter, and can perform distinction and segmentation of the fundus tissue. The polarization OCT uses light modulated into circularly polarized light as measuring beam for observing the sample to detect interfering light split as two orthogonal linear polarizations and generate the polarization OCT image (refer to International Patent Application WO2010/122118A1).

However, International Patent Application WO2010/122118A1 discusses nothing about a diagnostic support which is an original purpose of the polarization OCT, more specifically a method for effectively confirming exudates appearing on the retinal layer, so that the exudates cannot be effectively confirmed.

SUMMARY OF THE INVENTION

The present invention is directed an image processing apparatus and image processing method capable of displaying information about exudates on a display unit using information about polarization components acquired from a polarization OCT image so that a user can effectively confirm exudates.

According to an aspect of the present invention, an image processing apparatus configured to process a tomographic image indicating the polarization state of a subject, includes an acquisition unit configured to acquire a plurality of the tomographic images imaged at different times, an extraction unit configured to extract each depolarized area from the plurality of the tomographic images, and a display control unit configured to display information about each depolarized area on a display unit with the information associated with each other.

Further features of the present invention will become apparent from the following description of exemplary embodiments with reference to the attached drawings.

DESCRIPTION OF THE EMBODIMENTS

An imaging apparatus according to the present invention is applicable to subjects such as a subject's eye, a skin, and internal organs. The imaging apparatus according to the present invention is an ophthalmologic apparatus and an endoscope, for example. The following describes in detail an ophthalmologic apparatus according to the present exemplary embodiment as an example of the present invention with reference to the attached drawings.

[Overall Configuration of the Apparatus]

Figure 1:
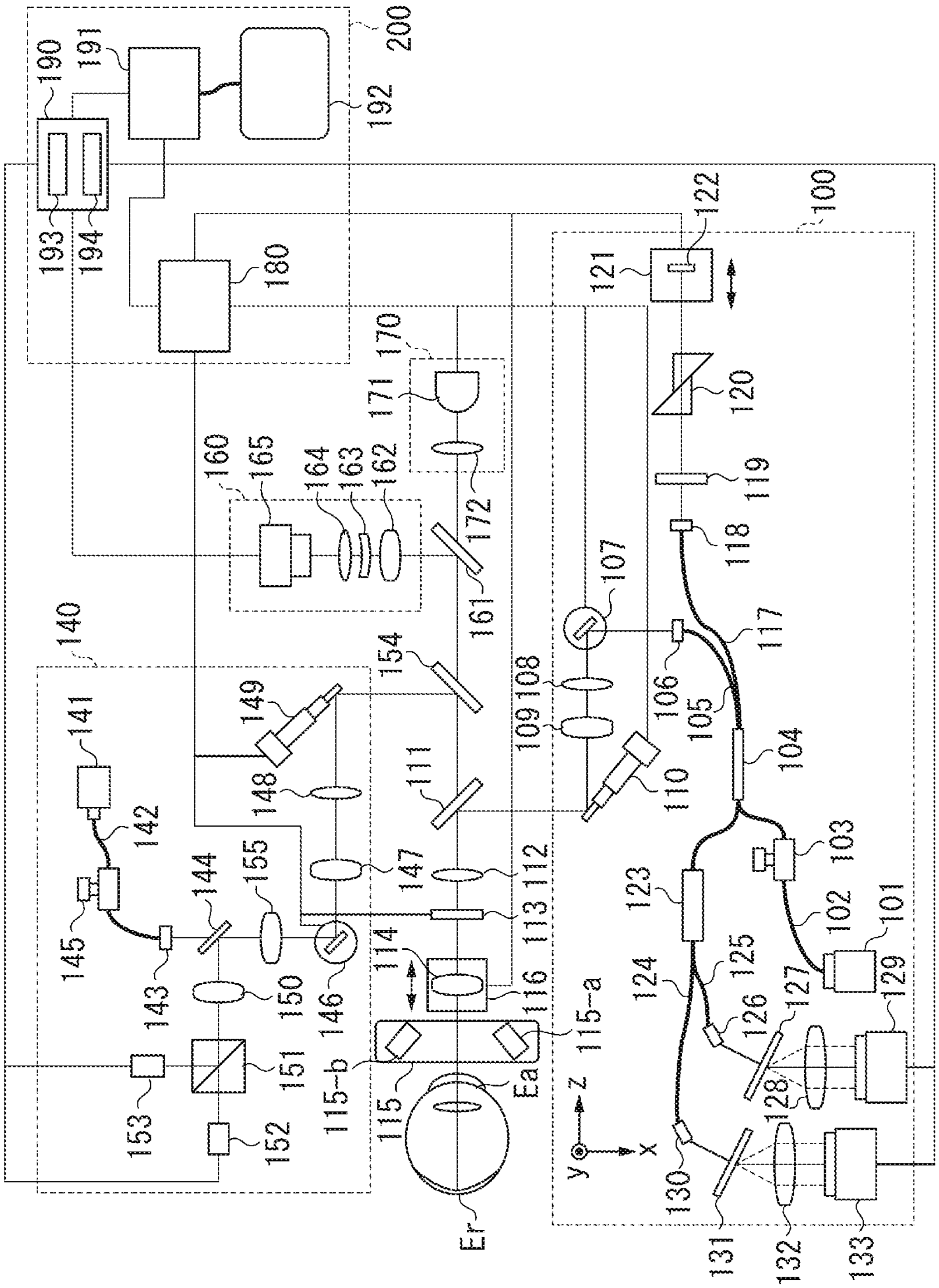
FIG. 1 is a schematic diagram illustrating an overall configuration of an image processing apparatus according to an exemplary embodiment.

FIG. 1 is a schematic diagram illustrating an overall configuration of an "ophthalmologic apparatus" which is an example of an imaging apparatus in the present exemplary embodiment. At least a part of a signal processing unit 190 described below can be regarded as an "image processing apparatus." In this case, the entire "ophthalmologic apparatus" can be regarded as an "ophthalmologic system", or the entire "imaging apparatus" can be regarded as an "imaging system".

The ophthalmologic apparatus includes an polarization sensitive OCT 100 (hereinafter referred to as PS-OCT), a polarization sensitive scanning laser ophothalmoscope 140 (hereinafter referred to as PS-SLO), an anterior eye imaging unit 160, an internal fixation lamp 170, and a control unit 200.

Alignment of the ophthalmologic apparatus is performed using an image at an anterior eye portion of the subject observed by the anterior eye imaging unit 160 with the internal fixation lamp 170 turned on and the subject's eye caused to gaze thereat. After the alignment is completed, the PS-OCT 100 and the PS-SLO 140 perform imaging of the fundus.

<Configuration of OCT 100>

The configuration of the OCT 100 is described.

A light source 101 is a super luminescent diode (SLD) light source low in coherence and emits light with a center wavelength of 850 nm and a band width of 50 nm, for example. Although the SLD is used as the light source 101, any light source which can emit low-coherent light such as an amplified spontaneous emission (ASE) light source, for example, may be used.

The light emitted from the light source 101 is guided to a fiber coupler 104 with a polarization holding function via a polarization maintaining (PM) fiber 102 and a polarization controller 103, and split into a measuring beam (hereinafter referred to as "measuring beam for a tomographic image" or "OCT measuring beam") and a reference beam corresponding to the measuring beam.

The polarization controller 103 is for adjusting the state of light emitted from the light source 101 to linear polarization. The branching ratio of the fiber coupler 104 is 90 (the reference beam) to 10 (the measuring beam).

The measuring beam is emitted as parallel light from a collimator 106 via a PM fiber 105. The emitted measuring beam reaches a dichroic mirror 111 via an X scanner 107 including a galvanometer mirror which scans the measuring beam in the horizontal direction at the fundus Er and a Y scanner 110 including a galvanometer mirror which scans the measuring beam in the vertical direction at lenses 108 and 109 and the fundus Er. The X and Y scanners 107 and 110 are controlled by a drive control unit 180 and can scan the measuring beam in a desired range of the fundus Er. The range in which the measuring beam is scanned on the fundus can be regarded as the acquisition range of the tomographic image, the acquisition position of the tomographic image, and the irradiation position of the measuring beam. The X and Y scanners 107 and 110 are examples of scanning unit for the PS-OCT and may be configured as a common XY scanner. The dichroic mirror 111 has a characteristic that reflects light with a wavelength of 800 nm to 900 nm and transmits the rest.

The measuring beam reflected by the dichroic mirror 111 passes through a λ/4 polarizing plate which is arranged with an angle of 45° tiled from P polarization to S polarization with an optical axis as a rotation axis via a lens 112 to shift the phase of the measuring beam by 90°, and is polarization controlled to a circularly polarized light. The λ/4 polarizing plate is an example of a polarization adjustment member for the measuring beam for adjusting the polarization state of the measuring beam. If the PS-SLO optical system described below is applied, the λ/4 polarizing plate 113 can be provided in a common optical path of a part of the PS-OCT optical system and apart of the PS-SLO optical system. This allows comparatively suppressing the dispersion of polarization state occurring on the image acquired by the PS-SLO optical system and the image acquired by the PS-OCT optical system. At this point, the scanning units for the PS-SLO and the PS-OCT are provided in positions conjugate to each other and can be provided in positions conjugate to the pupil of the subject's eye. The tilt of the λ/4 polarizing plate 113 is an example of state of the λ/4 polarizing plate 113 and an angle from a predetermined position with the optical axis of a polarization split face of a fiber coupler 123 incorporating a polarization beam splitter as a rotation axis, for example.

The λ/4 polarizing plate 113 can be attached and detached to and from the optical path. There may be a mechanical configuration for rotating the λ/4 polarizing plate 113 with the optical axis or an axis parallel to the optical axis as a rotation axis, for example. This makes it possible to realize a small apparatus which can simply switch between the SLO and PS-SLO optical systems. In addition, this makes it possible to realize a small apparatus which can simply switch between the OCT and PS-SLO optical systems.

The light incident on the subject's eye is polarization-controlled to a circularly polarized light by arranging the λ/4 polarizing plate tilted by 45°, however, the light may not be controlled to the circularly polarized light at the fundus Er depending on the characteristics of the subject's eye. For that reason, the tilt of the λ/4 polarizing plate can be fine-adjusted by controlling the drive control unit 180.

The measuring beam which is polarization-controlled to a circularly polarized light is focused on the retinal layer of the fundus Er via the anterior eye portion Ea of eye, which is the subject, by a focus lens 114 mounted on a stage 116. The measuring beam with which the fundus Er is irradiated is reflected and scattered by each retinal layer and returns to the fiber coupler 104 via the above optical path.

The reference beam branched by the fiber coupler 104 is emitted as a parallel light from a collimator 118 via a PM fiber 117. As is the case with the measuring beam, the emitted reference beam is polarization-controlled by a λ/4 polarizing plate 119 which is arranged at an angle of 22.5° tiled from P polarization to S polarization with an optical axis as a rotation axis. The λ/4 polarizing plate 119 is an example of a polarization adjustment member for the reference beam for adjusting the polarization state of the reference beam. The reference beam passes through a dispersion compensation glass 120, is reflected by a mirror 122 on a coherence gate stage 121, and returns to the fiber coupler 104. This means that the reference beam passes through the λ/4 polarizing plate 119 twice to cause linear polarization light to return to the fiber coupler 104.

The coherence gate stage 121 is controlled by a drive control unit 180 to cope with difference in eye's axial length. A coherence gate refers to a position corresponding to an optical path length of the reference beam in the optical path of the measuring beam. In the present exemplary embodiment, the optical path length of the reference beam is changed, however, a difference in an optical path length between the optical paths of the measurement and the reference beam has only to be changed.

The light returning to the fiber coupler 104 is combined with the reference beam to be interfering light (hereinafter referred also to as "combined light"). The interfering light is incident on the fiber coupler 123 incorporating the polarization beam splitter. The polarization beam splitter splits the interfering light into P and S polarized light which are different in a polarization direction with a split ratio of 50:50.

The P polarized light passes through a PM fiber 124 and a collimator 130, is separated by a grating 131, and received by a lens 132 and a line camera 133. Similarly, the S polarized light passes through a PM fiber 125 and a collimator 126, is separated by a grating 127, and received by a lens 128 and a line camera 129. The gratings 127 and 131 and the line cameras 129 and 133 are arranged in the direction according to each polarized light.

The light received by each of the line cameras 129 and 133 is output as an electric signal according to the strength of the light and received by a signal processing unit 190 being an example of a tomographic image generation unit.

The tilts of the λ/4 polarizing plates 113 and 119 can be automatically adjusted based on the tilt of polarization split face of the polarization beam splitter, but may be automatically adjusted with reference to a straight line connecting the center of optic disk of the fundus with the center of macula lutea of the fundus. It is desirable to have a tilt detection unit (not illustrated) for detecting the tilts of the λ/4 polarizing plates 113 and 119. The tilt detection unit can detect a present tilt and a predetermined tilt. Needless to say, the tilts of the λ/4 polarizing plates 113 and 119 may be detected based on the strength of the received light to adjust the tilts thereof so that a predetermined strength of light can be acquired. As described below, an object indicating the tilt is displayed on a graphic user interface (GUI) and a user may adjust the tilt using a mouse. The polarization beam splitter and the λ/4 polarizing plates 113 and 119 are adjusted with reference to the perpendicular direction as a polarization reference to acquire the similar effect.

<Configuration of PS-SLO 140>

The configuration of the PS-SLO 140 is described below.

A light source 141 is a semiconductor laser and emits light whose center wavelength is 780 nm, for example, in the present exemplary embodiment. The measuring beam emitted from the light source 141 (hereinafter referred to as "measuring beam for fundus image" or "SLO measuring beam") passes through a PM fiber 142, is polarization controlled to a linearly polarized light by a polarization controller 145, and emitted as parallel light from a collimator 143. The emitted light passes through a hole portion of a perforated mirror 144 and reaches a dichroic mirror 154 via a lens 155, an X scanner 146 including a galvanometer mirror which scans the measuring beam into the horizontal direction at the fundus Er, lenses 147 and 148, and a Y scanner 149 including a galvanometer mirror which scans the measuring beam into the vertical direction at the fundus Er. The X and Y scanners 146 and 149 are controlled by the drive control unit 180 and can scan a desired range on the fundus using the measuring beam. The X and Y scanners 146 and 149 are examples of the scanning unit for the PS-SLO and may be configured as a common XY scanner. The dichroic mirror 154 has a characteristic that reflects light with a wavelength of 760 nm to 800 nm and transmits the rest.

The measuring beam of liner polarization reflected by the dichroic mirror 154 passes through the same optical path as the measuring beam of the PS-OCT 100 and reaches the fundus Er.

The measuring beam with which the fundus Er is irradiated is reflected and scattered at the fundus Er, and reaches the perforated mirror 144 via the above-described optical path. The light reflected by the perforated mirror 144 passes through a lens 150, is split by a polarization beam splitter 151 into light different in polarization direction (P polarized light and S polarized light in the present exemplary embodiment), received by avalanche photo diodes (APD) 152 and 153, converted into a electric signal, and received by the signal processing unit 190, which an example of a fundus image generation unit.

The position of the perforated mirror 144 is conjugate to the position of a pupil of the subject's eye. The light passing through the periphery of the pupil among light in which the measuring beam with which the fundus Er is irradiated is reflected and scattered is reflected by the perforated mirror 144.

In the present exemplary embodiment, both of the PS-OCT and the PS-SLO use the PM fiber, however, the use of a single mode fiber (SMF) allows acquiring similar configuration and effect by controlling polarization using the polarization controller.

<Anterior Eye Imaging Unit 160>

The anterior eye imaging unit 160 is described.

In the anterior eye imaging unit 160, the anterior eye portion Ea is irradiated by an illumination light source 115 composed of light emitting diodes (LED) 115-*a* and 115-*b* emitting illumination light with a wavelength of 1000 nm. The light reflected by the anterior eye portion Ea reaches a dichroic mirror 161 via the lens 114, the polarizing plate 113, the lens 112, and the dichroic mirrors 111 and 154. The dichroic mirror 161 has a characteristic that reflects light with a wavelength of 980 nm to 1100 nm and transmits the rest. The light reflected by the dichroic mirror 161 is received by an anterior eye camera 165 via lenses 162, 163, and 164. The light received by the anterior eye camera 165 is converted into an electric signal and received by the signal processing unit 190.

<Internal Fixation Lamp 170>

The internal fixation lamp 170 is described.

The internal fixation lamp 170 includes an internal fixation-lamp display unit 171 and a lens 172. A plurality of light emitting diodes (LD) arranged in a matrix form is used as the internal fixation-lamp display unit 171. A position where to turn on the light emitting diodes is changed according to a site desired to be imaged by controlling the drive control unit 180. The light emitted from the internal fixation-lamp display unit 171 is guided to the subject's eye via the lens 172. The light emitted from the internal fixation-lamp display unit 171 has a wavelength of 520 nm and a desired pattern is displayed by the drive control unit 180.

<Control Unit 200>

The control unit 200 for controlling the entire apparatus is described below.

The control unit 200 includes the drive control unit 180, the signal processing unit 190, a display control unit 191, and a display unit 192.

The drive control unit 180 controls each unit as described above.

The signal processing unit 190 includes an image generation unit 193 and an image analysis unit 194. The signal processing unit 190 generates an image, analyzes the generated image, and generates visualization information of the analysis result based on the signals output from the line cameras 129 and 133, the APDs 152 and 153, and the anterior eye camera 165. The generation and analysis of an image are described below in detail.

The display control unit 191 displays on display unit 192 the images generated by the tomographic image generation unit and the fundus image generation unit and acquired by a fundus image acquisition unit (not illustrated) and a tomographic image acquisition unit (not illustrated) respectively on a display screen. The display unit 192 is a liquid crystal display, for example. The image data generated by the signal processing unit 190 may be transmitted by wire to the display control unit 191 or by wireless. In this case, the display control unit 191 can be regarded as an image processing apparatus. As an image system, the fundus image acquisition unit may include the SLO optical system, and the tomographic image acquisition unit may include the OCT optical system. In this specification, for the case of a subject except the subject's eye, a "fundus image (fundus luminance image)" may be paraphrased in a "planar image (planar luminance image)" and the "fundus image acquisition unit" may be paraphrased in a "planar image acquisition unit".

The display unit 192 displays display forms indicating various pieces of information described below under the control of the display control unit 191. The image data from the display control unit 191 may be transmitted by wire to the display unit 192 or by wireless. The display unit 192 is included in the control unit 200, however, the present invention is not limited thereto, and the display unit 192 may be provided separately from the control unit 200. Alternatively, a tablet may be provided, which is an example of a user portable apparatus into which the display control unit 191 and the display unit 192 are integrated. In this case, it is desirable to mount a touch panel function on the display unit to allow moving the display position of an image, expanding and reducing the image and changing the displayed image on the touch panel.

[Image Processing]

The image generation by the image generation unit 193 included in the signal processing unit 190 is described below.

The image generation unit 193 subjects the interference signals output from the line cameras 129 and 133 to a re-configuration processing used in a general spectral domain OCT (SD-OCT) to generate tomographic images corresponding to a first and a second polarized light which are two tomographic images based on each polarization component.

The image generation unit 193 reduces a fixed pattern noise from the interference signal. The fixed pattern noise is reduced in such a manner that a plurality of the detected A scan signals is averaged to extract the fixed pattern noise, and the extracted fixed pattern noise is subtracted from the input interference signal.

The image generation unit 193 converts the interference signal from wavelength to the number of waves and performs Fourier-transform thereof to generate a tomographic signal indicating a polarization state.

The interference signal of two polarization components is subjected to the above processing to generate two tomographic images.

The image generation unit 193 aligns the signals output from the APDs 152 and 153 in synchronization with the drive of the X and Y scanners 146 and 149 to generate fundus images corresponding to the first and the second polarized light which are two fundus images based on each polarization component.

<Generation of Tomographic Luminance Image or Fundus Luminance Image>

The image generation unit 193 generates the tomographic luminance image from the two tomographic signals.

The tomographic luminance image is basically the same as the tomographic image in the conventional OCT. The pixel value r is calculated from the tomographic signals $A_H$ and $A_V$ acquired from the line sensors 129 and 133 by an equation 1:

$$r=\sqrt{A_H^2+A_V^2} \quad \text{(Equation 1)}$$

Similarly, the image generation unit 193 generates the fundus luminance image from the two fundus luminance images.

Figure 2A:
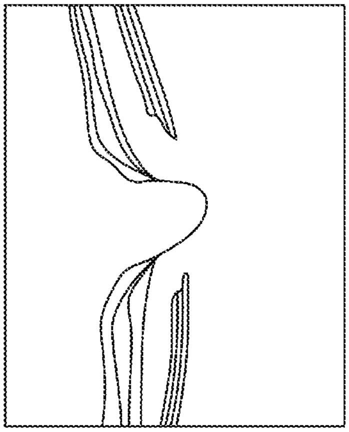
FIGS. 2A to 2E illustrate examples of images generated by a signal processing unit 190.

FIG. 2A illustrates an example of a luminance image of an optic disk portion.

The display control unit 191 may cause the display unit 192 to display the tomographic luminance image acquired by a conventional OCT method on the display unit 192 if the λ/4 polarizing plate 113 is removed from the optical path or the fundus luminance image acquired by a conventional SLO method on the display unit 192.

<Generation of Retardation Image>

The image generation unit 193 generates a retardation image from a tomographic image of polarization components orthogonal to each other.

A value δ of each pixel of the retardation image is a value indicating a ratio of influence of vertical and horizontal polarization components on the subject's eye in a position of each pixel forming the tomographic image. The value δ is calculated from the tomographic signals $A_H$ and $A_V$ by an equation 2:

$$\delta = \arctan\left[\frac{A_V}{A_H}\right] \quad \text{(Equation 2)}$$

Figure 2B:
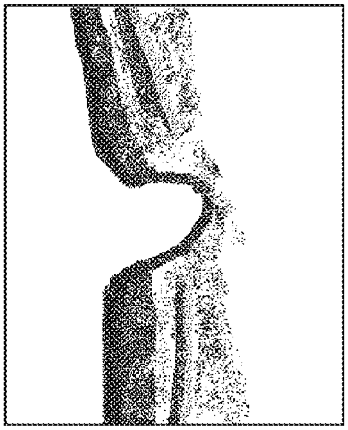

FIG. 2B illustrates an example of a retardation image of thus generated optic disk portion, and the retardation image can be obtained by the equation 2 for each B scan image. As described above, the retardation image refers to the tomographic image indicating a difference in influence of two polarizations on the subject's eye. In FIG. 2B, the value indicating the ratio is displayed in color as the tomographic image. Places where shading is thick are small in value indicating the ratio. Places where shading is thin are large in value indicating the ratio. For this reason, the generation of the retardation image allows a birefringent layer to be recognized. The details are as discussed in "E. Gotzinger et al., Opt. Express 13, 10217, 2005".

Similarly, the signal processing unit 190 can also generate the retardation image in the planar direction of the fundus based on the output from the APDs 152 and 153.

<Generation of Retardation Map>

The image generation unit 193 generates a retardation map from the retardation image acquired from a plurality of B scan images.

The image generation unit 193 detects a retinal pigment epithelium (hereinafter referred to as "RPE") in each B scan image. The RPE has the property of dissolving polarization, so that the distribution of retardation is examined along a depth direction without the range from an internal limiting membrane (hereinafter referred to as "ILM") to the RPE by each A scan and the maximum value of the retardation is taken as the representative value of the retardation in the A scan.

The image generation unit 193 performs above processing on all retardation images to generate a retardation map.

Figure 2C:
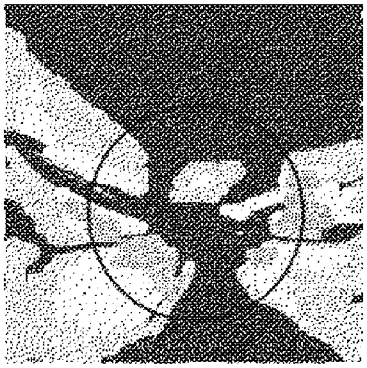

FIG. 2C illustrates an example of the retardation map of the optic disk portion. Places where shading is thick are small in value indicating the ratio. Places where shading is thin are large in value indicating the ratio. In the optic disk portion, a layer with birefringence is a retinal nerve fiber layer (hereinafter, referred also to as "RNFL"). The retardation map is an image indicating a difference in influence which two polarizations receive according to the birefringence of the RNFL and the thickness of the RNFL. For this reason, the value indicating the ratio is increased at a place where the RNFL is thick and decreased at a place where the RNFL is thin. Therefore, with the retardation map, the thickness of the RNFL all over the fundus can be recognized, and the retardation map can be used for the diagnosis of glaucoma.

<Generation of Birefringence Map>

The image generation unit 193 linearly approximates the value of the retardation δ in the range from the ILM to the RNFL in each A scan image of the previously generated retardation image and determines the tilt of the retardation δ as birefringence in a position on the retina of the A scan image. In other words, the retardation is the product of distance and birefringence in the RNFL, so that the values of depth and retardation in each A scan image are plotted to acquire a linear relationship. Therefore, if the tilt is acquired by linearly approximating the plot using the least squares method, the tilt is a value of the birefringence of the RNFL in the A scan image. All the retardation images are subjected to the processing to generate the map indicating birefringence.

Figure 2D:

FIG. 2D illustrates an example of the birefringence map of the optic disk portion. Because birefringence values are directly mapped, the birefringence map can describe a fiber structure as a change in birefringence if the fiber structure is changed even if the thickness of the RNFL is not changed.

[Generation of DOPU Image]

The image generation unit 193 calculates a Stokes vector S for each pixel from the acquired tomographic signals $A_H$ and $A_V$ and a phase difference $\Delta\phi$ between the tomographic signals using an equation 3.

$$S = \begin{pmatrix} I \\ Q \\ U \\ V \end{pmatrix} = \begin{pmatrix} A_H^2 + A_V^2 \\ A_H^2 - A_V^2 \\ 2A_H A_V \cos\Delta\phi \\ 2A_H A_V \sin\Delta\phi \end{pmatrix} \quad \text{(Equation 3)}$$

Where, the phase difference $\Delta\phi$ is calculated from phases $\phi_H$ and $\phi_V$ of each signal acquired when two tomographic signals are calculated as $\Delta\phi = \phi_V - \phi_H$.

The image generation unit 193 sets a window with a size of about 70 μm in the main scanning direction of the measuring beam and about 18 μm in the depth direction thereof in each B scan image, averages each element of a stroke vector calculated for each pixel by a number C in each window and calculates the degree of polarization uniformity (DOPU) of polarization in the window using an equation 4.

$$\text{DOPU} = \sqrt{Q_m^2 + U_m^2 + V_m^2} \quad \text{(Equation 4)}$$

Figure 2E:
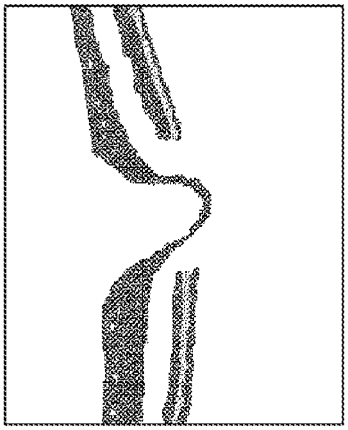

Where, $Q_m$, $U_m$, and $V_m$ are values in which the elements Q, U, and V of the stroke vector in each window are averaged. All the windows in the B scan image are subjected to the processing to generate the DOPU image of the optic disk portion illustrated in FIG. 2E. As described above, the DOPU image is the tomographic image indicating the degree of uniformity of two polarizations.

The DOPU is a value indicating the degree of uniformity of polarization and is the value near to 1 in a place where polarization is maintained, but is the value smaller than 1 in a place where polarization is dissolved and not maintained. Ina structure of a retina, the RPE has the property of dissolving polarization, so that the value is smaller than that in other areas in a portion corresponding to the RPE in the DOPU image. in FIG. 2, a place where shading is thin represents the RPE and a place where shading is thick represents the area of the retinal layer where change is maintained. The DOPU image images a layer canceling polarization such as the RPE, so that the DOPU image can more surely image the RPE than change in luminance even if the RPE is deformed due to disease.

Similarly, the signal processing unit 190 can also generate the DOPU image in the planar direction of the fundus based on the output from the APDs 152 and 153.

In the present specification, the tomographic image, the retardation image, and the DOPU image corresponding to the first and the second polarization described above are also referred to as a tomographic image representing the polarization state. Also in the present specification, the retardation map and the birefringence map described above are also referred to as a fundus image representing the polarization state.

[Processing Operation]

The processing operation of the image processing apparatus is described below.

Figure 3:
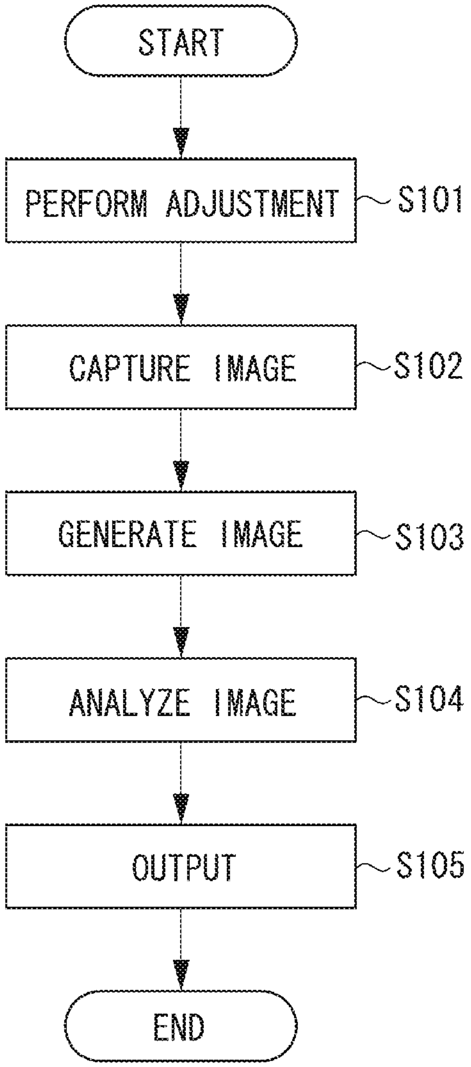
FIG. 3 is a flowchart illustrating a processing flow according to the exemplary embodiment.

FIG. 3 is a flow chart illustrating the processing operation of the image processing apparatus.

[Adjustment]

In step S101, the subject's eye is placed on the apparatus and the apparatus is aligned with the subject's eye. For the description of alignment, only specific processing of the present exemplary embodiment is described. The descriptions of alignment in the XYZ directions such as working distance, and the adjustment of focus and coherence gate are omitted because they are general.

<Adjustment of PS-OCT Imaging Position>

Figure 10:
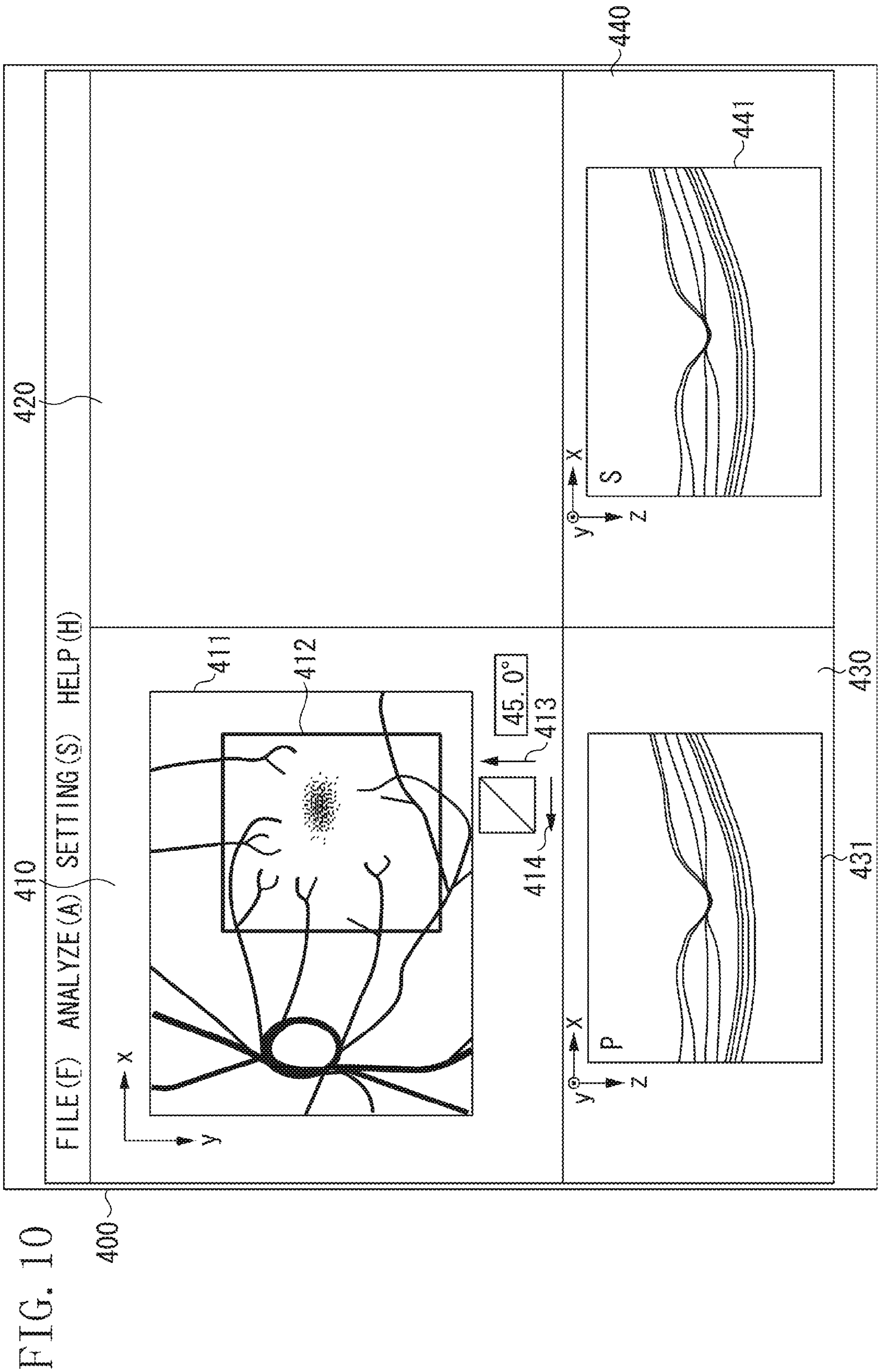
FIG. 10 is a display example illustrating a display screen of a display unit of the image processing apparatus according to the exemplary embodiment.

FIG. 10 illustrates a window 400 displayed in the display unit 192 during adjustment. A fundus image 411 imaged by the PS-SLO 140 and generated by the signal processing unit 190 is displayed in a display area 410 which is an example of a first display area and a frame 412 indicating the imaging range of the PS-OCT 100 is superimposed and displayed on the fundus image 411.

The imaging range is set under the control of the drive control unit 180 in such a manner that the imaging range is specified by a cursor displayed on the window 400 and by performing click and drug operation using an instruction apparatus (not illustrated) such as a mouse. In other words, the frame 412 is specified by the cursor and drug operation is performed to move the frame 412. With this operation, the drive control unit 180 controls the drive angle of the scanner to set the imaging range. The mouse according to the present exemplary embodiment is provided with a sensor which detects a movement signal when a mouse main body is two-dimensionally moved by a user's hand, for example, a left and a right mouse buttons for detecting the pressing by the user's hand, and a wheel mechanism which can be rotated back and forth and left and right between the left and the right mouse button. A display unit of the instruction apparatus may be provided with a touch panel function to specify an acquisition position on the touch panel.

<Adjustment of λ/4 Polarizing Plate>

The adjustment of the λ/4 polarizing plate is described below.

FIG. 10, instruction portions 413 and 414 are displays to be used for adjusting the angle of the λ/4 polarizing plate 113. The operator issues instructions using the instruction apparatus to adjust the angle of the λ/4 polarizing plate 113 under the control of the drive control unit 180. The instruction portion 413 is a display for instructing a counterclockwise adjustment. The instruction portion 414 is a display for instructing a clockwise adjustment. A numeric value displayed at the side of the instruction portions 413 and 414 indicates the present angle of the λ/4 polarizing plate 113. The display control unit 191 may arrange the instruction portion for adjusting the angle of the λ/4 polarizing plate 119 alongside of the instruction portion 413 and display the instruction portion on the display unit 192, or may display the instruction portion instead of the instruction portion 413 on the display unit 192.

The operator issues an instruction with a cursor using the mouse so that the luminance of the tomographic image of each polarization displayed in a display area 430, which is an example of a third display area, and a display area 440, which is an example of a fourth display area becomes equal to each other. It may be possible to display a peak luminance value along with the tomographic images 431 and 441 of respective polarizations or waveforms themselves of respective interference signals to perform adjustment while viewing them. The tomographic images 431 and 441 of each polarization are examples of the tomographic images corresponding to the first and the second polarization. It is desirable that a display form indicating the type of each image, in other words, a character "P" representing P polarization or a character "S" representing S polarization, for example, is superimposed on the tomographic images 431 and 441 of each polarization (or tomographic images 531 and 541, described below) and displayed. This can prevent the user from erroneously recognizing an image. It is needless to say that the character may be displayed above or at the side of the image without being superimposed on the images or displayed correspondingly with the image.

In this stage, there is no need for displaying anything in a display area 420 which is an example of a second display area. In the case of automatic adjustment, a display form indicating the present adjustment state, that is, a message "λ/4 polarizing plate is being adjusted", for example, may be displayed. The window 400 may display a display form indicating patient information such as the left and right eyes of the subject's eyes or indicating imaging information such as an imaging mode. It is desirable to repeat attachment and detachment of the λ/4 polarizing plate 113 to and from the optical path to alternately acquire the fundus luminance image and the tomographic image indicating the polarization state. With this operation, in an ophthalmologic apparatus as small as possible, the display control unit 191 can display the fundus luminance image in the display area 410 and display the tomographic image indicating the polarization state in the display area 420, for example.

It is desirable to perform adjustment in the following order: alignment adjustment using the anterior-eye portion image or a luminescent spot in a cornea; focus adjustment using the fundus image indicating the polarization state; coherence gate adjustment using the tomographic image indicating the polarization state; and adjustment of the λ/4 polarizing plate. A position where the tomographic image indicating the polarization state is acquired is desirably determined before the coherence gate adjustment using the tomographic image indicating the polarization state, however, the position may be determined at an initial setting to acquire the center area of the tomographic image indicating the polarization state. Thereby, the ophthalmologic apparatus can be easily adjusted so that the tomographic image indicating the polarization state targeting a finer and narrower area than the fundus image indicating the polarization state can be accurately and easily obtained. At this point, the λ/4 polarizing plate may be automatically adjusted upon the completion of the coherence gate adjustment or upon the input of a signal for acquiring the image indicating the polarization state. Needless to say, the λ/4 polarizing plate may be previously adjusted on an initial. setting screen in starting the ophthalmologic apparatus to eliminate the need for adjustment for each imaging.

If the λ/4 polarizing plate can be attached and detached to and from the optical path, it is desirable to perform adjustment in the following order: alignment adjustment using the anterior-eye portion image or a luminescent spot in a cornea; focus adjustment using the SLO fundus image; coherence gate adjustment using the OCT tomographic image; insertion of the λ/4 polarizing plate into the optical path; and adjustment of the λ/4 polarizing plate. Adjustment can thus be performed before acquiring the image indicating the polarization state, using the normal SLO fundus image and the OCT tomographic image which the user is accustomed to and can perform intuitively. The coherence gate may also be adjusted using the tomographic image indicating the polarization state of the PS-OCT after inserting the λ/4 polarizing plate after performing focus adjustment. At this point, the λ/4 polarizing plate may be automatically inserted into the optical path in response to completion of adjustment of the coherence gate or in response to completion of adjustment of focus, or the λ/4 polarizing plate may be automatically inserted into the optical path in response to the-input of a signal for acquiring the image indicating the polarization state.

The focus may be finely adjusted using the OCT tomographic image after coarsely adjusting the focus using the SLO fundus image.

All of such adjustments may be automatically performed in the above order or by the user adjusting the cursor to a slider corresponding to each adjustment displayed on the display unit and performing dragging operation. If the λ/4 polarizing plate is attached or detached, an icon for instructing the λ/4 polarizing plate to be attached or detached to and from the optical path may be displayed on the display unit.

<Imaging> to <Image Formation>

In step S102 and step S103 in FIG. 3, each of the light sources 101 and 141 emits the measuring beam. The line cameras 129 and 133, and the APDs 152 and 153 receive the return beam from the fundus Er, and the image generation unit 193 generates each image as described above.

<Analysis>

The luminance value of the tomographic image of ill eye can be lower than that of the tomographic image of healthy eye due to influence of illness. A retinal layer may be overlooked or erroneously detected due to the influence. For this reason, in step S104, the image analysis unit 194 detects each layer of the retinal layer using information about a place where the polarization state is randomized calculated by the image generation unit 193 in step S103.

Figure 4:
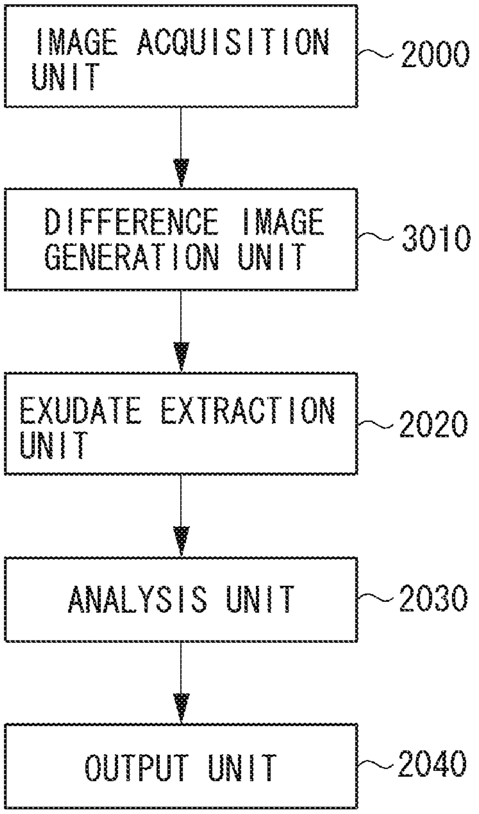
FIG. 4 is a schematic diagram illustrating an example of an image analysis unit.

FIG. 4 illustrates a configuration of the image analysis unit 194. In FIG. 4, an image acquisition unit 2000 is an acquisition unit for acquiring the tomographic image indicating the polarization state generated by the image generation unit 193. The acquisition unit can also be configured to acquire an image from an external server.

A difference image generation unit 3010 and an exudate extraction unit 2020 are extraction units. The difference image generation unit 3010 extracts the RPE as an example of a predetermined layer by analyzing the continuity of a polarization canceling material and subtracts the RPE from the tomographic image indicating the polarization state. The exudate extraction unit 2020 subtracts the predetermined layer from the image and then extracts the exudates.

An analysis unit 2030 acquires information about the position and size of the exudate acquired by the exudate extraction unit 2020. An output unit 2040 outputs processing results to the display control unit 191. The analysis unit 2030 and the output unit 2040 may be included in the display control unit 191.

Figure 5:
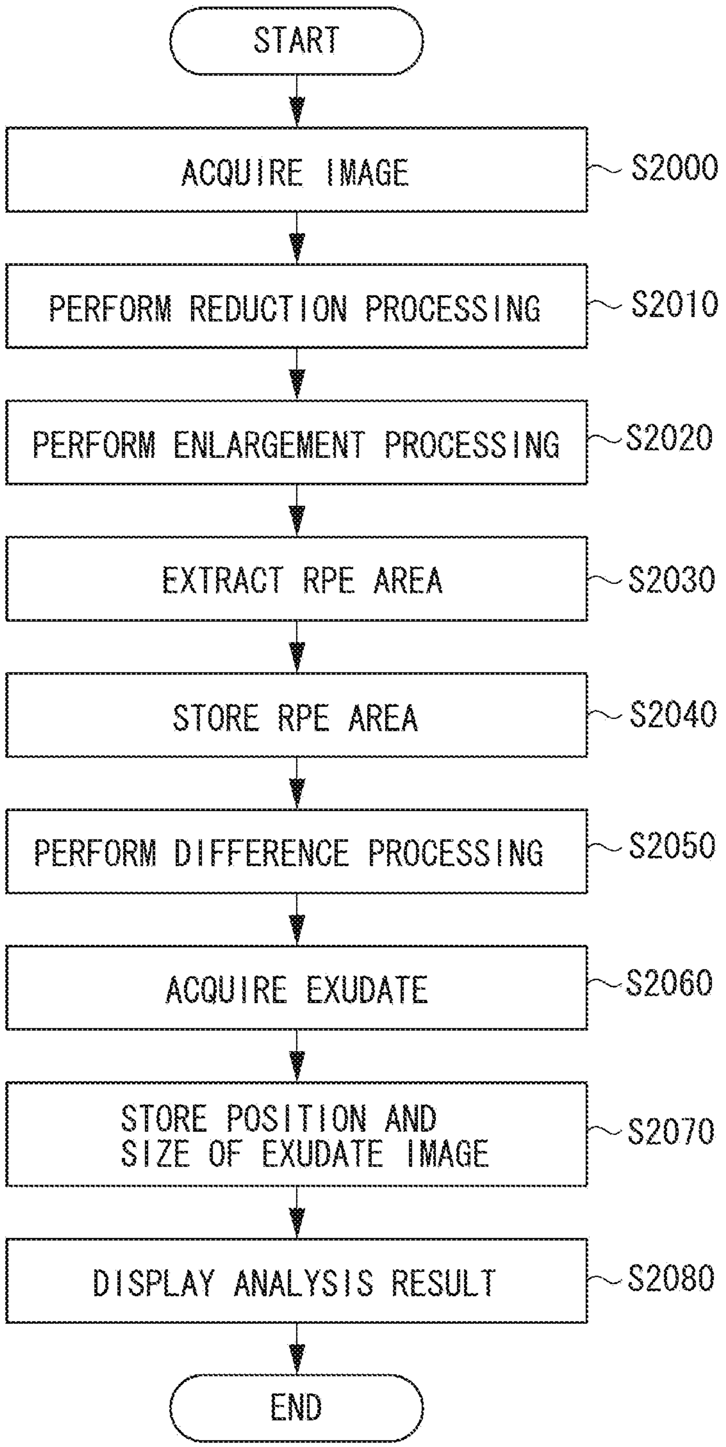
FIG. 5 is a flow chart illustrating a flow of processing according to the exemplary embodiment.

FIG. 5 is a flowchart illustrating a detailed flow of the processing in step S104. The processing in step S104 is described in detail according to the flow of the processing in FIG. 5.

In step S2000, an image acquisition unit 2000 acquires a plurality of three-dimensional tomographic images each indicating a polarization state, which are imaged at different times. A DOPU image acquired by calculating the DOPU using the equation 4 can detect the position of the RPE layer as the predetermined layer because the RPE cancels the polarization state in the retinal layer. The RPE has a layer structure, so that the RPE exists as a mass with a certain capacity or more. On the other hand, exudates often scatter and are smaller than the layer structure such as the RPE.

In step S2010, the difference image generation unit 3010 subjects the area in a pixel value range in a predetermined range to reduction processing by using a filtering processing with a filter such as a morphological filter. For example, a dilation processing is performed. With this processing, exudates disappear. The difference image generation unit 3010 enlarges the reduced image with a reverse processing. For example, an erosion processing is performed. The reverse processing refers to processing to expand an image by the amount equal to the reduction amount. This can provide the layer structure of the RPE. In steps S2030 and S2040, the difference image generation unit 3010 subjects the layer structure of the RPE to binary processing, for example, and stores the area with the predetermined value or more as the area of the RPE layer.

In step S2050, the difference image generation unit 3010 subjects the enlarged image to difference processing with respect to the tomographic image indicating the original polarization state. With this processing, in step S2060, an depolarized area except the RPE layer is acquired (extracted) as exudates. Each image in a depolarized area and information about an area such as the extracted exudates are stored while being associated with the tomographic image indicating the polarization state. Information about imaging time including imaging date and time is also associated with the tomographic image indicating the polarization state. For this reason, each image in the area where the polarization is randomized and information about an area such as the extracted exudates are associated with the imaging time and stored in the storage unit.

The analysis unit 2030 acquires the coordinates of center of gravity in the depolarized area such as exudates acquired from each image. A circumscribed area of the depolarized area such as exudates is acquired and a size of the depolarized area such as exudates is acquired as size. In step S2070, the coordinates of center of gravity in the depolarized area and a size of the depolarized area such as exudates are associated with images such as exudates, and information about the position is associated with the imaging time and stored in the storage unit.

<Output>

Output processing performed in step S105 of the generated images and analysis results is described below. In the output processing according to the present exemplary embodiment, information acquired in step S104 is effectively displayed.

Figure 6:
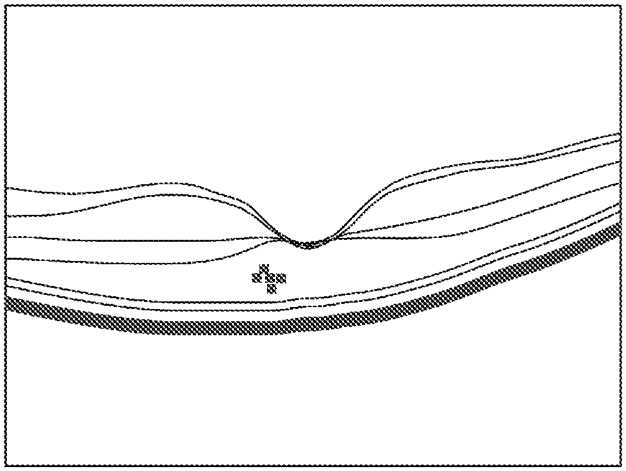
FIG. 6 is an example of display on a display screen of a display unit of the image processing apparatus according to the exemplary embodiment.

When the image generation unit 193 and the image analysis unit 194 in the signal processing unit 190 finish the generation and analysis of each image, the display control unit 191 generates output information based on the results, outputs the output information to the display unit 192 and displays the output information thereon. FIG. 6 is an example in which the display control unit 191 superimposes the image area of the extracted exudates on a two-dimensional tomographic image and displays it on the display unit 192.

Figure 7:
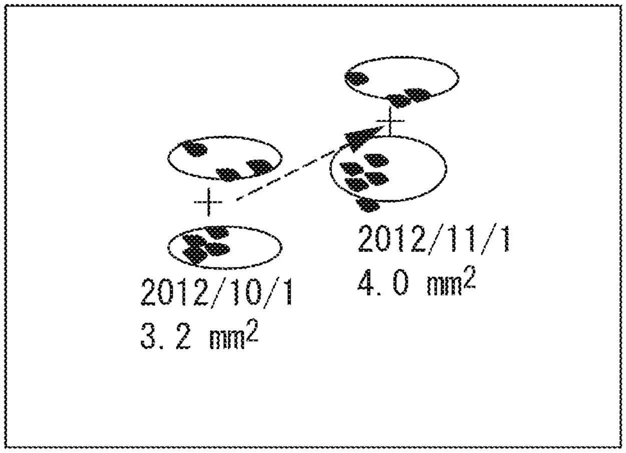
FIG. 7 is an example of display on the display screen of the display unit of the image processing apparatus according to the exemplary embodiment.

The analysis unit 2030 performs accumulation processing on the three-dimensional tomographic image, aligns it with the fundus image, which is a planar image, and associates information about the depolarized area such as the exudates extracted by the extraction unit with the coordinates of the fundus image, and stores the information. The display control unit 191 causes the image in the depolarized area, which is stored in the storage unit and imaged at different times, to correspond to the coordinates of the fundus image, which is a planar image, and displays the image on the display unit 192 as changing image. In this case, a color to be displayed for each corresponding imaging time is changed and displayed on the display unit 192 to make it clear how the depolarized area such as exudates is changed with time. Furthermore, the imaging time corresponding to a changing image is associated therewith and displayed to make it clear how the depolarized area such as exudates is changed with time. Moreover, the position and size of the center of gravity in the depolarized area such as exudates for each imaging time are displayed together to make it understandable how the size and the position are changed with time. FIG. 7 illustrates an example in which an image in an area where the polarization imaged at different imaging times is randomized is displayed correspondingly to the coordinates of the planar image, and the position and size of the center of gravity for each imaging time are displayed together on the display unit. In this case, the image is superimposed onto the fundus image, which is a planar image and displayed make it easy to perform comparison with the fundus image.

Figure 8:
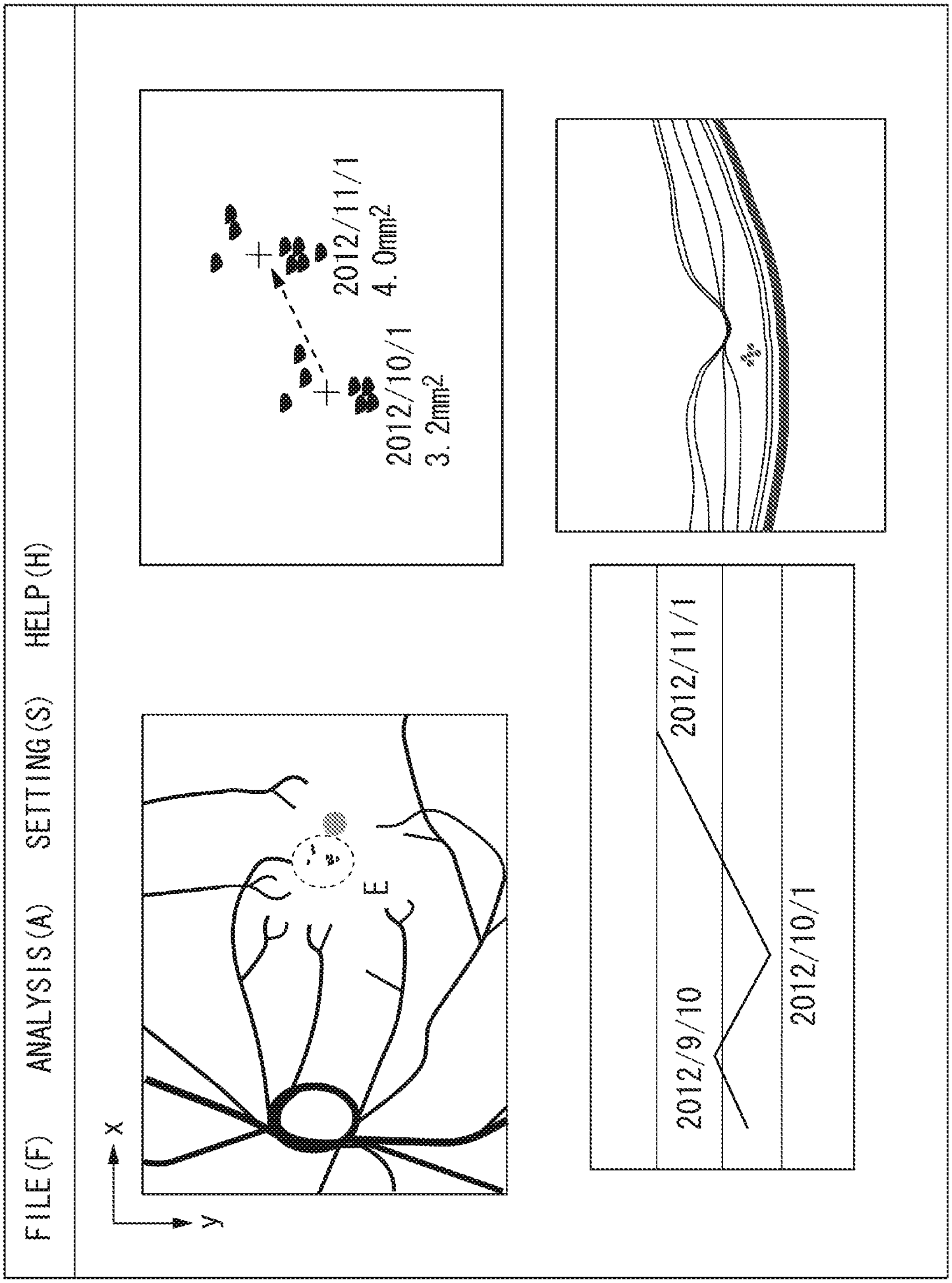
FIG. 8 is an example of display on the display screen of the display unit of the image processing apparatus according to the exemplary embodiment.

The upper left chart in FIG. 8 illustrates the fundus image. The upper right chart therein illustrates an image in an depolarized area is displayed correspondingly to the coordinates of the planar image and a changing image in which the position and size of the center of gravity for each imaging time are displayed together. The lower left chart illustrates a position image displaying the center of gravity as a position of the depolarized area correspondingly to the coordinates of the planar image and imaging time. The lower right chart illustrates the tomographic image crossing the area E where the polarization is randomized such as macula and exudates in the upper left chart. The display control unit 191 displays the images having thus different pieces of information alongside of each other on the display unit 192 to allow observing easily how the depolarized area such as exudates is changed with time.

MODIFICATION EXAMPLE 1

Figure 9:
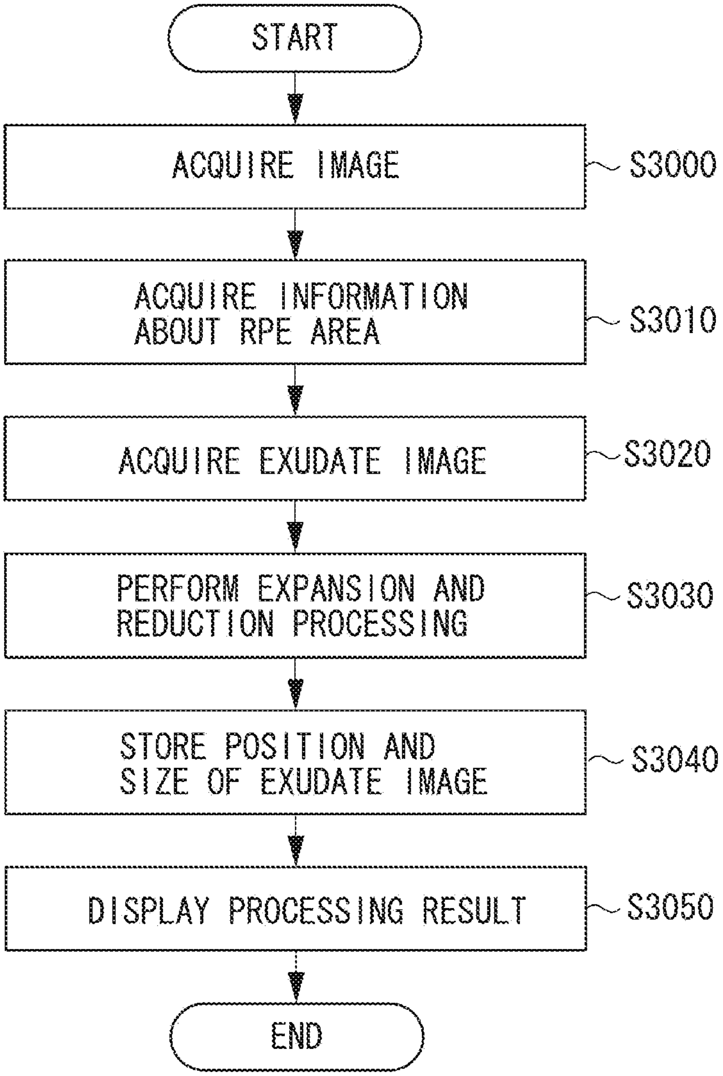
FIG. 9 is a flow chart illustrating a flow of processing according to the exemplary embodiment.

FIG. 9 is a flowchart illustrating a flow of processing in a modification example in which information about a depolarized area such as exudates is extracted.

In step S3000, the image acquisition unit 2000 acquires a plurality of three dimensional tomographic images, which are imaged at different times, each indicating the polarization state. In steps S3010 and S3020, an area extraction unit extracts information about a stored RPE layer area, removes the information about the RPE layer area from each of the three dimensional tomographic images to acquire a pixel value range in the predetermined range as information about the depolarized area such as exudates.

The analysis unit 2030 performs a processing for expanding and reducing the depolarized area such as exudates acquired from each image. In steps S3010 and S3020, the depolarized area such as exudates is extracted as an area with a certain degree of size by this processing. The analysis unit 2030 acquires the coordinates and the size of center of gravity in this area and stores them in the storage unit. A circumscribed area of the depolarized area such as exudates is acquired and a size of the depolarized area such as exudates is acquired as size. In step S3040, the coordinates of center of gravity in the depolarized area and a size of the depolarized area such as exudates are associated with images such as exudates, and information about position is associated with the imaging time and stored in the storage unit. In step S3050, the generated images and the analysis results are output.

[Other Exemplary Embodiments]

The present invention is realized by executing the following processing. Software (programs) realizing the functions of the above exemplary embodiments is supplied to a system or an apparatus via a network or various types of storage media, and a computer (or a central processing unit (CPU) or a micro processing unit (MPU)) of the system or the apparatus reads the programs and performs processing.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-235484 filed Oct. 25, 2012, which is hereby incorporated by reference herein in its entirety.

What is claimed is:

1. An image processing apparatus configured to process a tomographic image indicating the polarization state of a fundus of an eye, the image processing apparatus comprising:

an acquisition unit configured to acquire a plurality of the tomographic images imaged at different times;

an extraction unit configured to extract each depolarized area from an area excluding a Retina Pigment Epithelium (RPE) layer in the plurality of the tomographic images; and a display control unit configured to display information about each depolarized area extracted by the extraction unit on a display unit with the information associated with each other.

2. The image processing apparatus according to claim 1, wherein the display control unit associates images in each depolarized area with imaging times corresponding to the respective images in each area and displays the images on the display unit.

3. The image processing apparatus according to claim 1, wherein the subject is the area including a fundus and the extraction unit extracts an depolarized area from the area excluding the area of a predetermined layer in the fundus.

4. The image processing apparatus according to claim 3, wherein the extraction unit subjects an area in a pixel value range in a predetermined range of a tomographic image indicating the polarization state to reduction and expansion processing to extract a predetermined layer.

5. The image processing apparatus according to claim 1, wherein the extraction unit extracts an area in a predetermined pixel value range as an depolarized area.

6. The image processing apparatus according to claim 1, wherein the display control unit displays on the display unit an image in each depolarized area as a changing image displayed in a position to which the planar image of the subject corresponds on the display unit.

7. The image processing apparatus according to claim 1, wherein the display control unit displays on the display unit a position in an depolarized area as a position image associated with the imaging time on the display unit.

8. The image processing apparatus according to claim 1, wherein the display control unit further displays on the display unit an image in each depolarized area, as the image superimposed onto the planar image of the subject.

9. The image processing apparatus according to claim 8, wherein the display control unit displays an image in each depolarized area in color according to an imaging time.

10. The image processing apparatus according to claim 7, wherein the extraction unit extracts a center of gravity in the area acquired by subjecting an area in a pixel value range in a predetermined range of a tomographic image indicating the polarization state to a reduction and an expansion processing as a position in an depolarized area.

11. The image processing apparatus according to claim 1, wherein the extraction unit further acquires the size of the depolarized area, and the display control unit associates images in each of the depolarized area with the size corresponding to the images in each of the area, and displays the images on the display unit.

12. An image processing method for processing a tomographic image indicating a polarization state of a fundus of an eye, the tomographic image being acquired based on light in which a return light from a subject irradiated with a measuring beam is combined with a reference beam corresponding to the measuring beam and which is different in polarization from each other, the image processing method comprising:

acquiring a plurality of the tomographic images imaged at different times;

extracting ach depolarized area from an area excluding a Retina Pigment Epithelium (RPE) layer in the plurality of the tomographic images; and displaying information about each depolarized area extracted by the extracting step on a display unit with the information associated with each other.

13. A storage medium storing a program for causing a computer to execute each step of the image processing method according to claim 12.

14. The image processing apparatus according to claim 1, wherein the tomographic images are imaged by a polarization sensitive OCT (optical coherence tomography) apparatus.

* * * * *